(12) United States Patent
Auberger

(10) Patent No.: US 7,935,153 B2
(45) Date of Patent: May 3, 2011

(54) JOINT DEVICE

(75) Inventor: Roland Auberger, Vienna (AT)

(73) Assignee: Otto Bock Healthcare IP GmbH & Co. KG., Duderstadt (DE)

( * ) Notice: Subject to any disclaimer, the term of this patent is extended or adjusted under 35 U.S.C. 154(b) by 52 days.

(21) Appl. No.: 12/293,319

(22) PCT Filed: Mar. 15, 2007

(86) PCT No.: PCT/DE2007/000499
§ 371 (c)(1),
(2), (4) Date: Sep. 17, 2008

(87) PCT Pub. No.: WO2007/107150
PCT Pub. Date: Sep. 27, 2007

(65) Prior Publication Data
US 2009/0076618 A1 Mar. 19, 2009

(30) Foreign Application Priority Data

Mar. 17, 2006 (DE) .......................... 10 2006 012 716

(51) Int. Cl.
A61F 2/68 (2006.01)
A61F 5/00 (2006.01)
(52) U.S. Cl. ................ 623/43; 623/46; 602/16; 403/129
(58) Field of Classification Search .............. 623/39–52; 606/5, 16, 20–24, 62–63; 403/9, 129
See application file for complete search history.

(56) References Cited

U.S. PATENT DOCUMENTS

| 5,549,712 | A | | 8/1996 | Gammer et al. | |
|---|---|---|---|---|---|
| 5,873,847 | A | | 2/1999 | Bennett et al. | |
| 6,159,248 | A | * | 12/2000 | Gramnas | 623/44 |
| 6,471,664 | B1 | * | 10/2002 | Campbell et al. | 602/16 |

FOREIGN PATENT DOCUMENTS

| DE | 295807 | 3/1915 |
|---|---|---|
| DE | 329908 | 12/1920 |
| DE | 9320708 | 12/1994 |
| EP | 1159936 | 12/2001 |
| GB | 2244006 | 11/1991 |

OTHER PUBLICATIONS

International Search Report on PCTDE2007/000499, mailed Apr. 7, 2007, 3 pgs.

* cited by examiner

Primary Examiner — Bruce E Snow
(74) Attorney, Agent, or Firm — Holland & Hart, LLP

(57) ABSTRACT

A joint device for an orthoses or prostheses includes an upper part, a lower part mounted on the upper part in such a way as to turn about a pivot axis, and braking means that brakes or blocks a pivoting movement of the lower part relative to the upper part. The braking means includes a spiral spring arranged between two contact surfaces and is mounted such that it can be braced in the direction of the contact surfaces about a rotation axis parallel to the pivot axis.

20 Claims, 8 Drawing Sheets

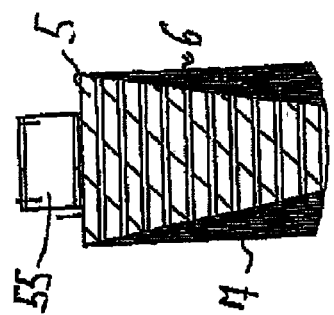
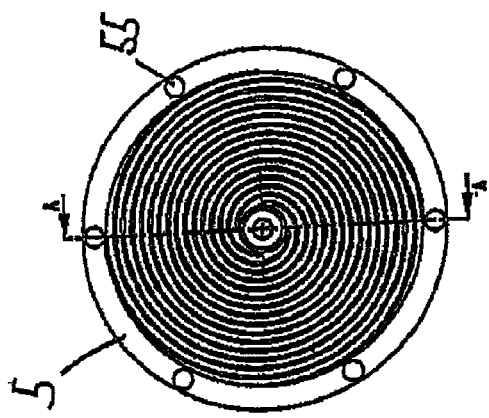
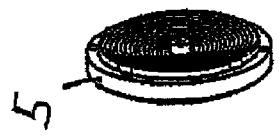
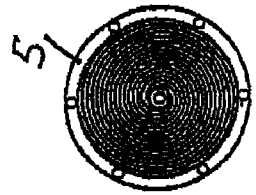
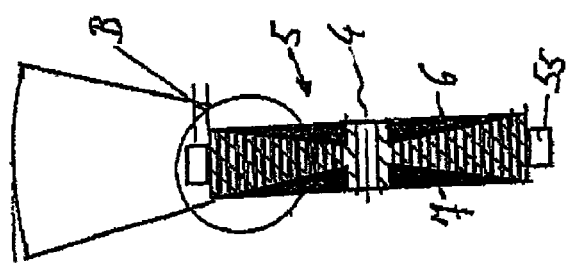

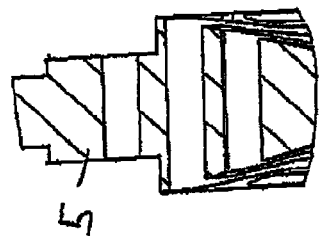
Fig. 7b
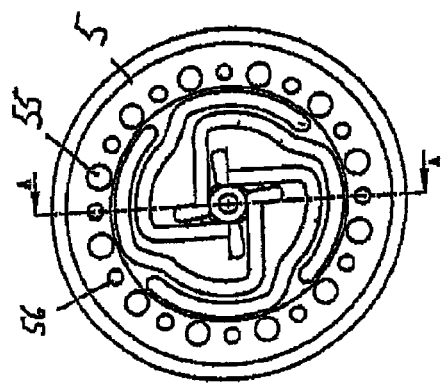
Fig. 7
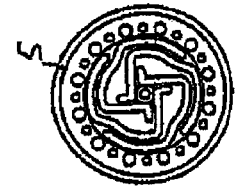
Fig. 7c
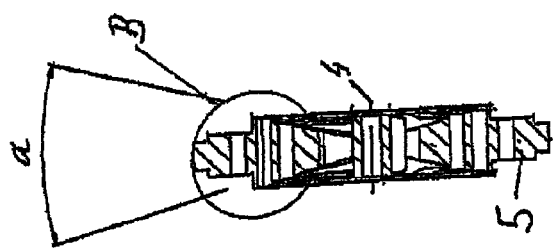
Fig. 7a

JOINT DEVICE

CROSS-REFERENCE TO RELATED APPLICATION

This application is a national stage application, filed pursuant to 35 USC §371, of PCT/DE2007/000499 filed Mar. 15, 2007, which claims priority to DE102006012716.1 filed Mar. 17, 2006, both of which are herein incorporated by reference in their entirety.

TECHNICAL FIELD

The invention relates to a joint device for orthoses or prostheses with an upper part, a lower part mounted on the upper part in such a way as to turn about a pivot axis, and braking means that brakes or blocks a pivoting movement of the lower part relative to the upper part.

BACKGROUND

Joint devices for orthoses and prostheses, which allow two prosthesis or orthosis components to be pivotable relative to each other, are known in the prior art. In a knee joint, for example, it is desirable to be able to obtain a damping in the swing phase and in the stance phase.

In another example, a joint device arranged in a single-axis shoulder joint is intended to allow an arm prosthesis or orthosis to be locked against falling. The same applies to the arrangement of the joint device in an elbow joint.

To configure braking means in these joints, various configurations are known, including positive locking in predetermined catch positions and hydraulic damping or braking of the movements. Such hydraulic controls are technologically very complex, however, and are disadvantageous in terms of the space they take up and their weight.

SUMMARY

An object of the present invention is to develop a joint device which can be opened or blocked with a low switching force and which at the same time requires very little space. In particular, the medial-lateral extent is intended to be kept as small as possible in order to ensure that the joint device, when used in an orthosis, can be worn discreetly under clothing.

A joint device according to embodiments of the invention for an orthoses or prostheses includes an upper part, a lower part pivotally mounted on the upper part to turn about a pivot axis, and braking means that brakes or blocks pivoting movement of the lower part relative to the upper part. The braking means includes, in one embodiment, a spiral spring arranged between two contact surfaces and is mounted such that it can be braced in the direction of the contact surfaces about a rotation axis parallel to the pivot axis such that the lateral flanks of the spiral spring come into contact with the contact surfaces when braced in their direction. In this way, it is possible for a very high braking moment to be built up by friction at very low switching forces and switching paths. The spiral spring, permits a very small overall size in the medial-lateral direction, even if a relatively large diameter is utilized. As a result of the bracing of the spiral spring in the direction of the contact surfaces, the individual spiral turns would, but for the contact surfaces, migrate in the direction of the contact surfaces. However, the contact surfaces cause the spiral turns to be wedged such that a braking or blocking moment occurs. By means of the wedging effect, the bracing is reinforced such that a self-reinforcing system is obtained. If a relative movement of the upper part and lower part occurs counter to the direction of spiral winding, the turns of the spiral move away from the contact surfaces such that a virtually unimpeded movement occurs as long as friction from the spring pretensioning is not so great that the opening movement is countered.

In a development of the invention, the contact surfaces are contoured, in particular with a radially conical or radially curved design, to increase the friction surface and to correspond to the successive radially outward turns of the spiral spring. In this way, a progressive braking action is obtained. The spiral spring may in this case be contoured according to the contact surfaces to provide the greatest possible friction surface between the contact surfaces and the flanks of the spiral spring. A conical or constantly curved configuration of the contact surfaces and of the spiral spring contour permits an additional wedging effect, which provides a great increase in force. Discontinuous cross-sectional geometries are likewise provided, e.g. multiple conical or curved contours, similar to that of a Christmas tree. In this way, the overall width can be reduced at a given wedge angle.

A particularly compact structure is permitted if the rotation axis of the spiral spring coincides with the pivot axis of the joint.

In a conical configuration of the contact surfaces, an angle of between 10° and 50° is preferred. Smaller angles may increase the risk of self-locking, while greater angles may increase the overall size in the medial-lateral direction and reduce self-reinforcement.

The bracing of the spiral spring may be adjustable, and in its rest position, the spiral spring may lie in contact with the contact surfaces. This ensures that, in the pivoting direction that is to be blocked, the self-initiating and reinforcing braking effect permits a reliable braking action, even if, to move the joint device counter to this direction, a certain moment has to be applied to overcome the initial braking action of the spiral spring.

In a development of the invention, the spiral spring is coupled to an actuator that braces or relaxes the spiral spring to actively control the joint device. For example, free mobility may be provided by relaxation of the spiral spring, that is to say a widening or contraction of the spiral spring away from the contact surfaces. On the other hand, sufficient bracing in the direction of the contact surfaces can provide a constant and reliable locking of the joint device or braking of the pivoting movement.

The actuator is preferably a servo type motor which, to increase the adjusting force and bracing of the spiral spring in or away from the direction of the contact surfaces, can be coupled to a lever, which acts on the spiral spring. In a starting position, the lever can be spring-loaded in the direction of locking to permit wear compensation. This may be achieved by a tension spring. To provide a reliable braking or locking failsafe in the event of failure of the actuator, the spiral spring may be pretensioned counter to the actuator in the locking direction. If the actuator fails, the spiral spring automatically turns in the direction of the contact surfaces, which results in an initial braking action that is increased by the self-reinforcing caused by the bracing of the spiral spring against the contact surfaces. In this way, it is possible to block a pivoting direction in the event of failure of the actuator. In the case of a knee joint or a knee-joint orthosis, the flexion would be blocked in order to avoid unintended buckling.

A development of the invention, includes a sensor device that measures moments, angles of the upper and lower parts relative to each other, and/or forces acting on the joint device. This sensor device is coupled to a control unit which, as a function of the measured variables or parameters, activates the actuator and braces the spiral spring against (or releases it from) the contact surfaces. In this way, the braking means is blocked or triggered as a function of load and position, such that the joint device is braked in a manner adapted to a particular situation. For example, if a knee prosthesis orthosis user stumbles, the braking means can be activated and the joint device locked such that unintended buckling is prevented. The flexion of the knee can in this way be limited in a specified manner.

In another development of the invention, the actuator is coupled to a control unit which, via myoelectric signals, activates or deactivates the actuator. Thus, joints can be locked or unlocked in a specific position by means of myoelectric signals.

In yet another embodiment a device for detecting the spatial orientation of the upper part and/or of the lower part is coupled to the actuator. A device for detecting the accelerations of the upper part and/or lower part, or of devices secured thereto, can also be coupled to the actuator. In this way, it is possible for the orthosis/prosthesis, or other device in which the joint device is fitted to be controlled with the aid of an absolute angle signal, that is to say an orientation either of the upper part or of the lower part to the perpendicular. From the position of the upper part and lower part relative to each other, the joint angle (for example the knee angle) is known such that the absolute spatial orientation both of the upper part and the lower part (and/or of the devices secured thereto) is also known. The device can therefore be fitted as an absolute angle sensor on the upper part or the lower part or on a device secured thereto. In this way, it is possible to control the actuator on the basis of information on the spatial orientation of the joint device or of the system in which the joint device is arranged. It is likewise possible to carry out this control on the basis of the accelerations that occur and are measured. Thus, the brake can be activated or disengaged as a function of the absolute angle and of the accelerations that occur.

A multi-turn design of the spiral spring provides particularly easy adjustability. An associated loss of friction surface can be compensated by increasing the diameter of the spiral spring and contact surfaces.

By using a nonlinear spiral geometry, it is possible to obtain a progressive braking action. It is likewise possible to vary the actuating moment via the number of spiral windings. The more windings a spiral spring has, the longer the actuating travel, but a very good adjustment of the braking moment may be accomplished. To permit a certain tolerance of the setting and gentle activation, a contact surface can be mounted so as to be axially displaceable to a limited extent. The spiral geometry is not limited to continuously curved free spaces or spiral turns. It is also possible to provide spiral turns that have varying cross sections, pitches, orientations or the like. Block-like elements can also be provided.

BRIEF DESCRIPTION OF THE DRAWINGS

An illustrative embodiment of the invention is explained in more detail below with reference to the figures, of which:

FIGS. 6, 6a, 6b and 6c show different views of a multiple-thread Euler spiral spring;

FIGS. 7, 7a, 7b and 7c show different views of a nonlinear spiral spring; and

DETAILED DESCRIPTION

Figure 1:
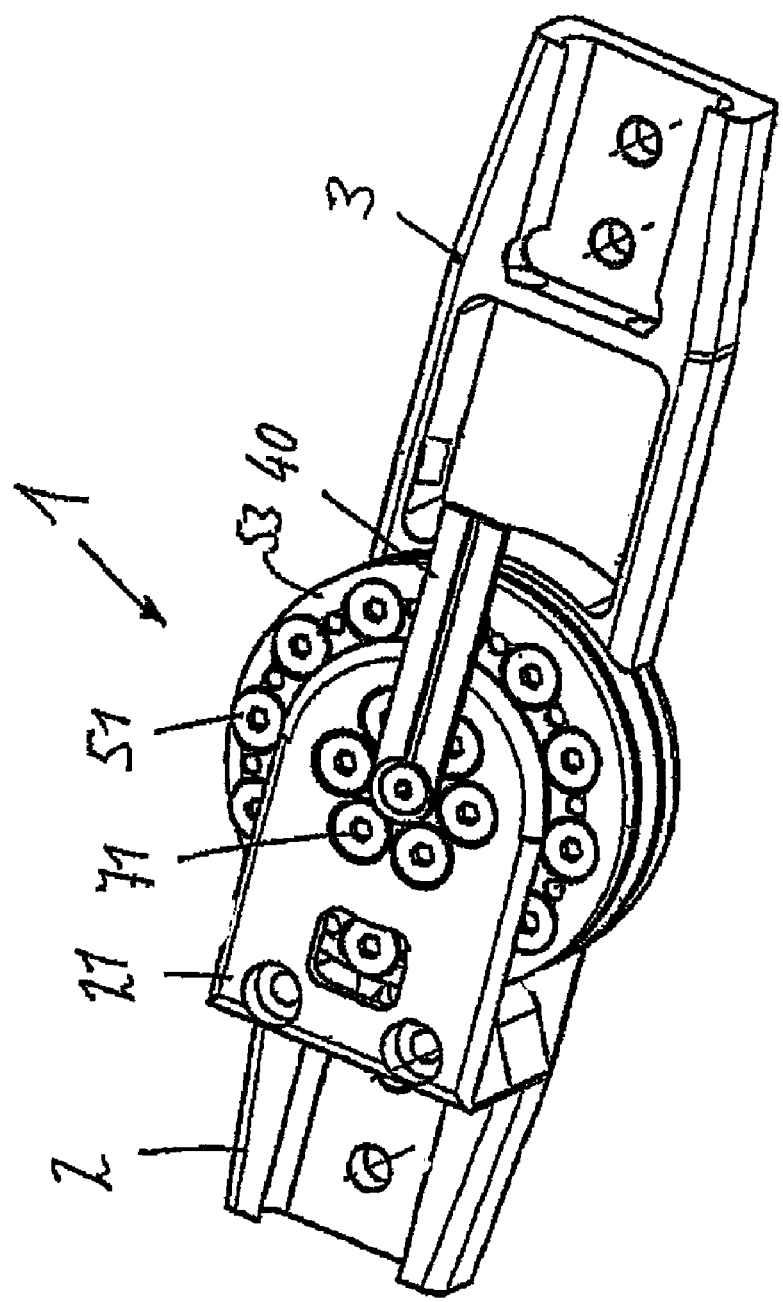
FIG. 1 shows a joint device in an assembled state.

A top view of a joint device 1 with an upper part 2 and a lower part 3 in an assembled state is shown in FIG. 1. The designations "upper part" and "lower part" do not connote any technical or spatial limitation to a specific arrangement, and instead an upper part can be arranged both at the proximal end and also at the distal end of a prosthesis or orthosis, the same applying accordingly to the lower part.

The upper part 2 has an L-shaped bracket 21, which is connected to, screwed onto or placed on the upper part 2 in an axially displaceable manner. A contact surface, which is not shown in this figure, is securely screwed onto the bracket 21 via screws 71. An actuating lever 40 projects from the bracket 21 in the direction of the lower part 3 and can be pivoted in both directions about a pivot axis 4 (see FIG. 2) by an actuator 41. The lever 40 is mounted so as to be pivotable relative to the upper part 2 and moves a spiral spring (see FIG. 3), which is secured in a rotationally fixed manner on the lower part 3 via screws 51 on the lower part 3. The upper part 2 and the lower part 3 can be secured on fastening elements of orthoses or prostheses.

Figure 2:
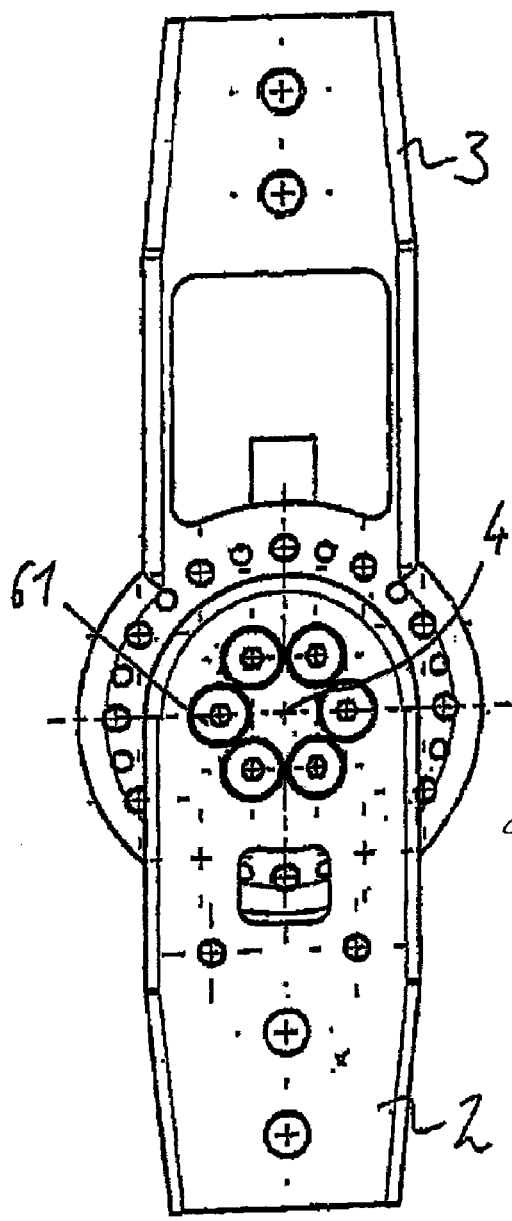
FIG. 2 shows a bottom view of a joint device according to FIG. 1.

A bottom view of the joint device 1 is shown in FIG. 2. The upper part 2 forms a support surface on which the second contact surface is mounted in a rotationally fixed manner via screws 61 and connected to form a functional unit. The lower part 3 is pivotable relative to the upper part 2 about a central pivot axis 4. A head piece in the shape of a circle is formed on the lower part 3, and the spiral spring is secured on said head piece via the screws 51.

Figure 3:
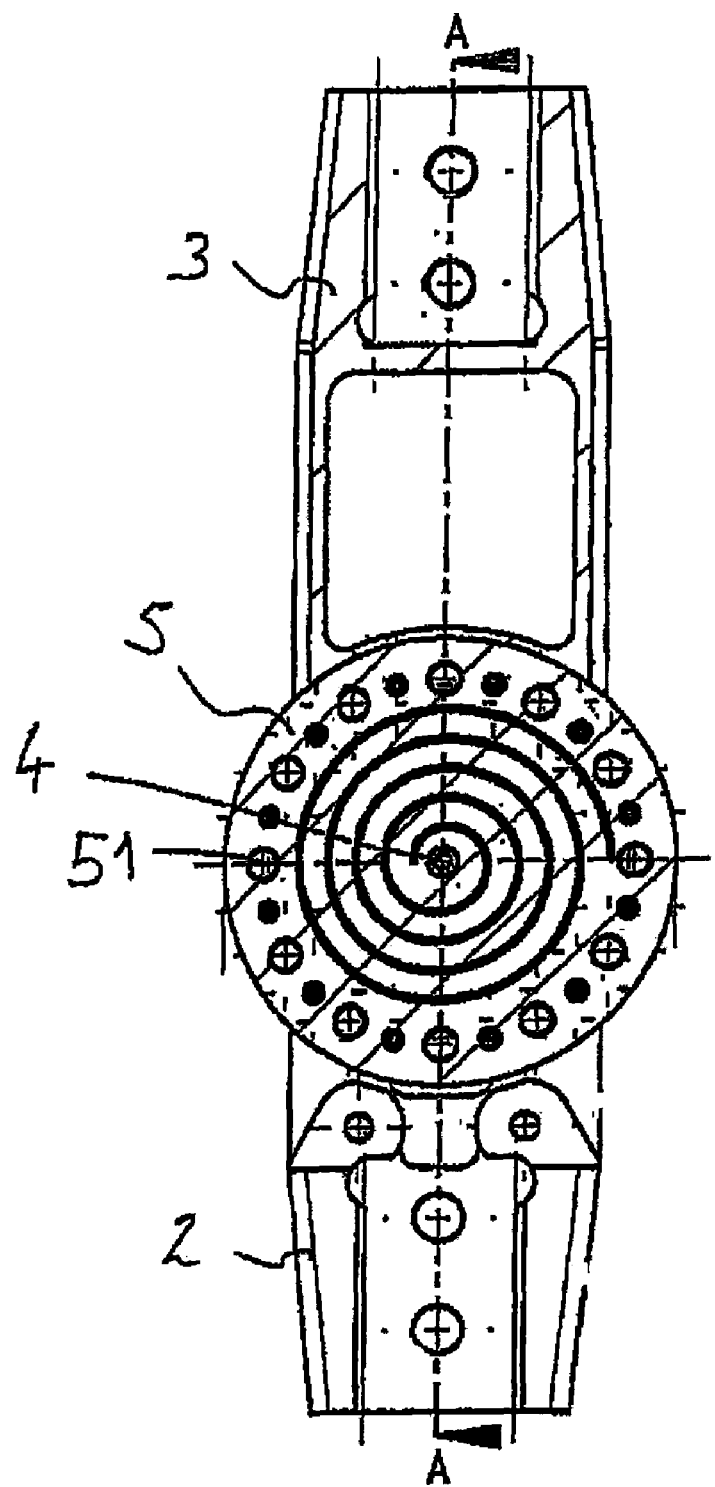
FIG. 3 shows a top view of a partially sectioned joint device.

An embodiment of the spiral spring 5 is shown in FIG. 3, which shows a sectional view through the upper part 2, the lower part 3 and the spiral spring 5. The bracket 21, the lever 40 and the upper, circular cover 53 are not shown.

Figure 4:
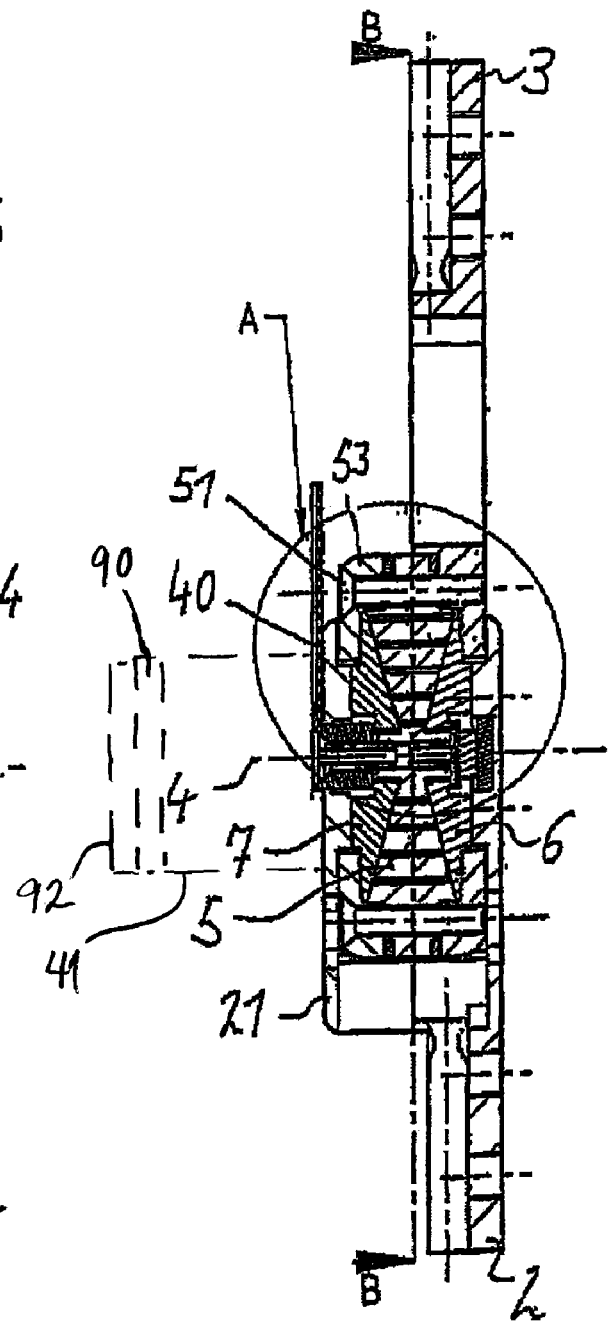
FIG. 4 shows a sectional view through a joint device fitted in place.
Figure 5:
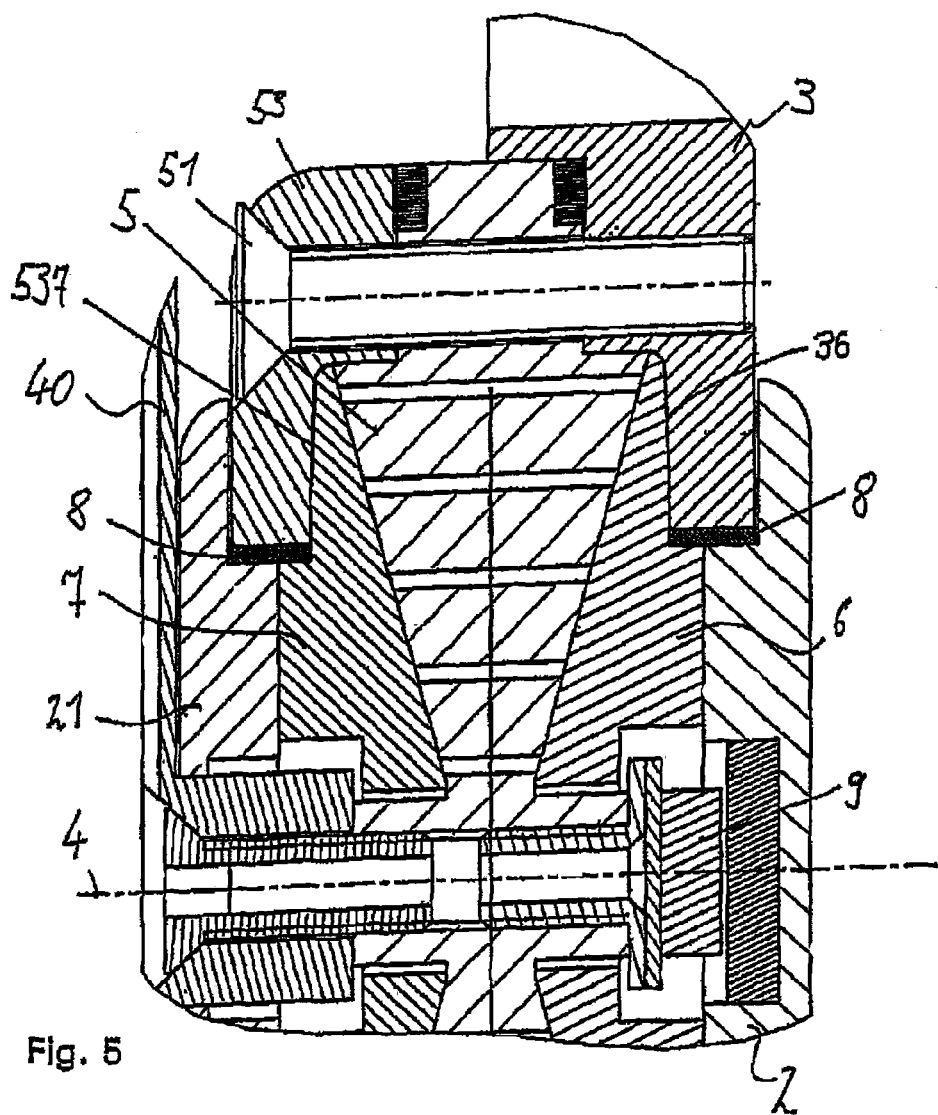
FIG. 5 shows an enlarged view of the detail A from FIG. 4.

The spiral spring 5 is mounted in a rotationally fixed manner on the lower part 3 via the screws 51 distributed about the circumference. It has a circular cross section with a single-thread spiral turn that extends inwardly in a spiral shape from the outside to the rotation axis 4, in a counterclockwise direction. As shown in FIGS. 4-5, parallel to and coincident with the pivot axis 4 the spiral spring 5 can be braced by actuation of the lever 40 counterclockwise in the direction of winding, such that the spiral spring 5 contracts inwardly in the direction of the rotation axis 4. The individual spiral turns migrate inwardly and then bear on the contact surfaces 6, 7, which are mounted in a rotationally fixed manner on the upper part 2 via the screws 61, 71 (FIGS. 1-2). Depending on the design of the contact surfaces 6, 7 and of the spiral spring 5, it is possible to achieve a braking action upon rotation in or counter to the direction of winding.

The structure and mode of action of the joint device 1 illustrated in FIG. 4. In the sectional view according to FIG. 4, the upper part 2 and the lower part 3 are secured on each other in such a way as to be pivotable relative to each other about the pivot axis 4. On the upper part 2, with the bracket 21 secured thereon via screws or bolts, contact surfaces 6, 7 are mounted in a rotationally fixed manner via the screws 61, 71. The contact surfaces 6, 7 have a conical contour and are arranged relative to each other in such a way that a wedge space that widens conically outward is formed. Arranged in this wedge space is the spiral spring 5, which is secured in a rotationally fixed manner on the lower part 3 by the screws 51 distributed about its circumference. The spiral spring 5 bears directly on the lower part 3 and on the cover 53. The lever 40 is likewise mounted so as to be pivotable about the rotation axis 4, which is also the axis of bracing, and it acts on the center of the spiral spring 5. If the lever 40, as shown in FIG. 1, is actuated in the counterclockwise direction, the spiral spring 5 is braced inwardly. The individual spiral turns with their conical contour attempt to migrate inwardly. However, the lateral limits formed by the contact surfaces 6, 7 act as brake disks, which prevent inward movement. Specifically, the lateral flanks of the spiral spring 5 wedge themselves against the contact surfaces 6, 7, as a result of which a braking moment or blocking moment is obtained. If, by contrast, the lever is activated in the clockwise direction counter to the direction of winding, the spiral turns widen outward. In this way, the friction between the lateral spiral surfaces and the contact surfaces 6, 7 is reduced or eliminated, such that there is reduced contact or no contact between the spiral spring 5 and the contact surfaces 6, 7. The joint, or the joint device 1, can thus be moved freely. If a blocked joint, or a blocked joint device 1, is moved counter to the direction of winding of the spiral spring 5, the friction between the side faces of the spiral spring 5 and the contact surfaces 6, 7 causes a widening of the spiral turns, such that the joint is able to move freely in this direction. However, the blocked joint is automatically blocked in an opposite direction of movement.

In the principle shown, the normal force needed to build up the braking or blocking moment acts perpendicular to the respective wedge face. In order to reduce the loads on the structural parts, such as the spiral spring 5 and the contact surfaces 6, 7, at a predetermined braking moment, multiple friction surfaces may be utilized. In the illustrated embodiments, two contact surfaces 6, 7 are provided. When the joint device 1 is blocked, these contact surfaces 6, 7 are forced apart and thus rub on the spring 5.

Figure 8:
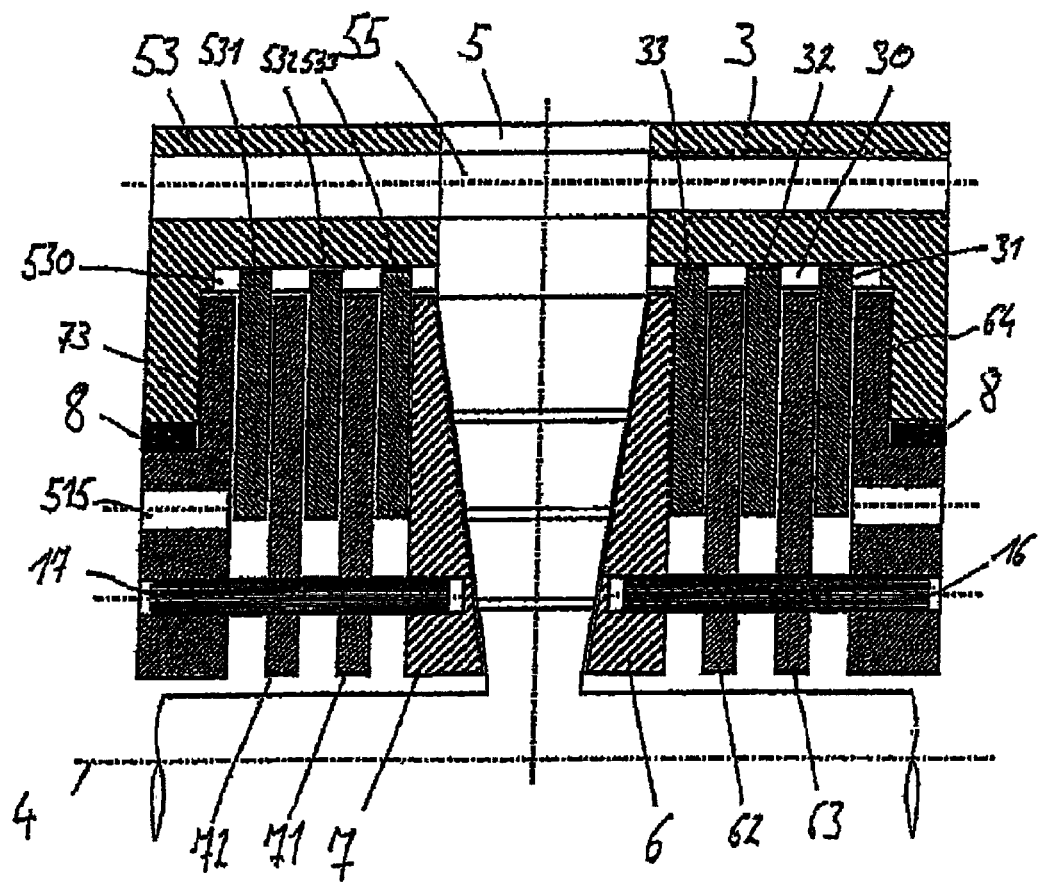
FIG. 8 shows a variant of the joint device in a partial view.

If the two contact surfaces 6, 7 are mounted so as to be axially displaceable to a limited extent, the radially inwardly directed movement of the spiral turns also causes further friction of the outer friction surfaces 36, 537 (See FIG. 5) of the contact surfaces 6, 7 on the lower part 3 and the circular cover 53. This results in a total of four brake surfaces which, at a predetermined braking moment, relieve the spring 5. The number of friction surfaces can be further increased by connecting the contact surfaces 6, 7 or the lower part 3 and cover 53 to a stack of plates, as is shown in FIG. 8. It is likewise possible for a plurality of contact surfaces and spiral springs to be mounted axially alongside one another. If two spiral springs with different directions of winding are provided, the joint can be blocked simultaneously in both directions of movement.

Figure 9:
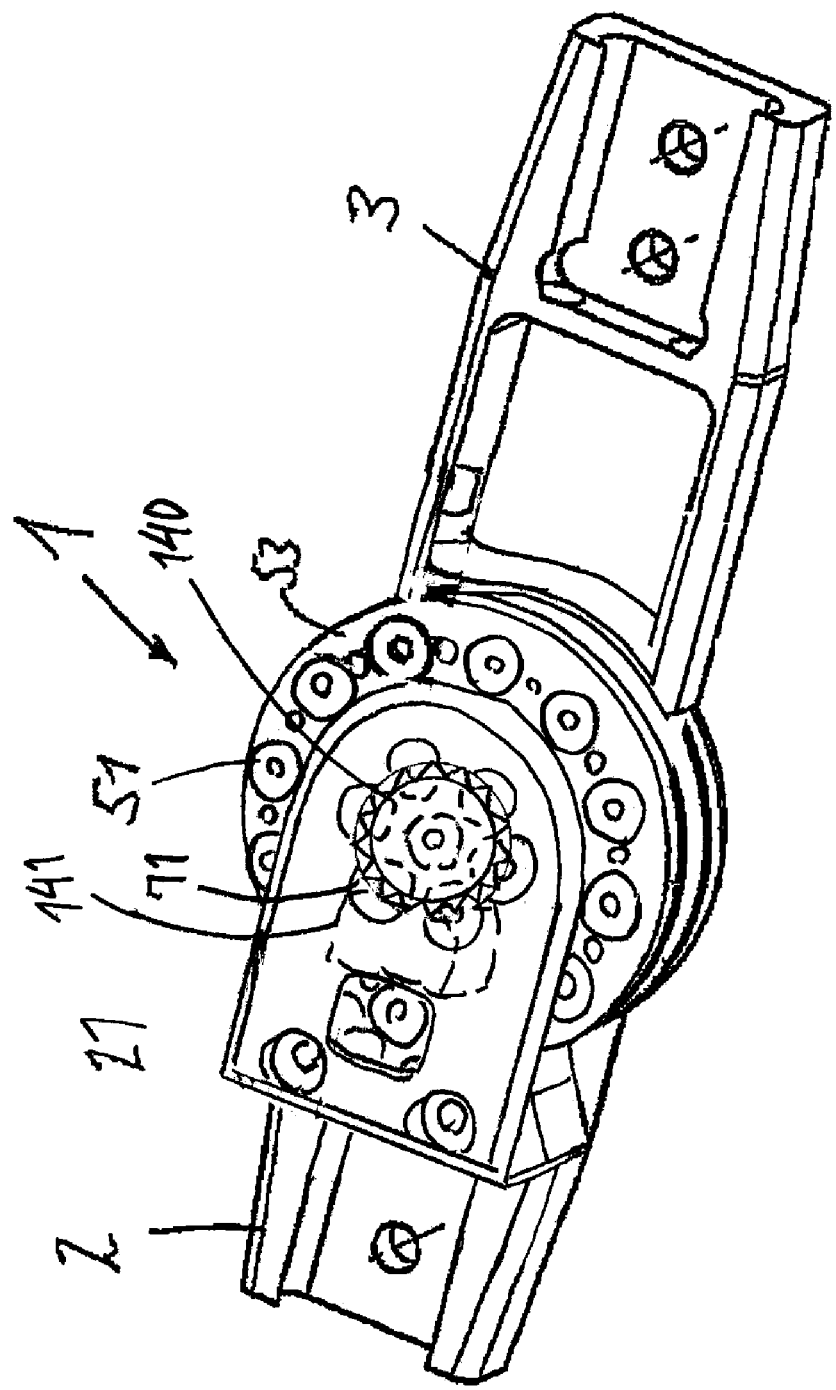
FIG. 9 shows another joint device in an assembled state.

The spiral spring 5 can be braced or released via the lever 40, as a result of which the joint, or the joint device 1, is either opened or blocked. A toothed wheel 140 (see FIG. 9) or a segment of a toothed wheel can also serve as lever 40. By way of a toothed gearing, a servomotor 141 (see FIG. 9) acting as actuator 41 can then be coupled directly to the toothed wheel 140 and thus to the spiral spring or springs, as a result of which the required installation space can be reduced. Adaptation to changing force conditions can be achieved by changing the gear ratio instead of by changing the lever length of an actuating lever.

In the partial view in FIG. 5, a radial sliding bearing 8 is also provided Between the upper part 2, bracket 21 and the lower part 3, and bears on end faces of the contact surfaces 6, 7, the upper part 2 and the bracket 21. The radial bearing 8 does not have to bear on the end faces, so long as it is secured against excessive axial movements. In this way, a sliding about the pivot axis 4 is made possible when the spiral spring 5 is not braced. FIG. 5 also shows an angle sensor 9, which senses the angle position or spatial orientation of the upper part 2 relative to the lower part 3 and sends these data to a control device 90 (see FIG. 4), which in turn activates an actuator 41, for example a servomotor. The joint device 1 can be blocked or opened in this way. A moment sensor can also be integrated in the upper part 2 or preferably in the lower part 3 of the structure.

A sensor device 90 (see FIG. 4), which may include the angle sensor 9 or other sensors such as a moment sensor, may measure at least one of forces, moments and the angle of the upper and lower parts 2, 3 relative to each other. The sensor device 90 may be coupled to a control until 92 (see FIG. 4) which, as a function of measured variables or parameters, activates the actuator 41 and braces the spiral spring 5. The sensor 90 may detect a spatial orientation of at least one of the upper part 2 and lower part 3 that are coupled to the actuator 41. The sensor 90 may detect accelerations of at least one of the upper part 2 and lower part 3 of the joint device 1, or of a prosthesis or orthosis secured to the joint device 1 that are coupled to the actuator 41.

Instead of being connected via the screws, 51, the cover 53 can be screwed directly onto the lower part 3 via a thread to protect against twisting. Like the screws 51, the thread can be used to set the gap size and to hold the parts together.

In order to avoid unwanted bracing, it may be necessary for the upper part 2, and the bracket 21 secured thereon, to permit an axial play, such that the two brake or contact surfaces 6, 7 can be axially displaced relative to each other to a slight extent. Provision is then made for the bracket 21 to be secured with play on the upper part 2 or for them to be connected to each other via two bolts that permit axial displacement.

The geometry of the spiral curve of the spiral spring 5 has a strong influence on the characteristics of the joint device 1. Spirals with many windings have a longer actuation path than spirals with few windings, but the achieved braking moment can be much more finely adjusted. Nonlinear spiral geometries are possible, for example, to achieve a progressive braking action or in order to optimize the loading of the spiral spring.

To reduce the actuating moment via the lever 40, several windings can be cut parallel to one another to form a spiral with multiple turns as shown in FIG. 6.

In a knee-joint orthoses or prostheses, the joint device 1 may be set in a Locking mode which prevents the joint from being freely pivotable in the event of a failure of the actuator 41. This can be achieved by pretensioning the actuating lever 40 in a locked position, for example, via a spring. The opening of the joint device or braking means then takes place actively counter to a spring force, such as a pretensioning force via the spiral spring 5. As an alternative to a pretensioning via the spiral spring 5, it is possible to provide a separate counter spring, which also provides automatic wear compensation. The opening of the joint device 1 then takes place actively counter to this counter spring force. If the pretensioning counter to the actuator 41 is in the middle of the moment range of interest, the braking moment to be achieved can be increased further or weakened.

It is likewise possible to provide a greater number of contact surfaces 6, 7, for example, stacked one behind another as in a multi-plate coupling, to further reduce the load of the spiral spring 5. Instead of a straight conical design of the contact surfaces 6, 7, it is likewise possible to provide a curvature in order to permit a particular increase in the braking moment in the event of an inward shifting of the spiral turns.

If the contact surfaces 6, 7 are designed such that they form a wedge space that tapers radially outward, the directions of rotation must accordingly be reversed, since the bearing on the contact surfaces 67 can be effected, and the braking moment obtained, by widening the spiral spring 5.

With the embodiments shown, the joint device can be easily opened under load by a motor-driven actuator or alternatively by a manual actuation. In an emergency, and if an actuator fails, the joint device may be locked in one pivoting direction if, in the starting position, the spiral spring 5 is in contact with the contact surfaces 6, 7. By a pivoting the upper part 2 and lower part 3 relative to each other, a braking moment is obtained and the braking action is increased by a wedging effect.

In an alternate embodiment, it is possible for two spiral springs acting in opposite directions to be arranged axially alongside each other, such that a brake can be obtained that is active in both pivoting directions and that requires few structural parts and can be switched in both directions of movement under load.

The joint device described above can also be used in components slipping as often as required, and it can therefore also be used for override clutches or reverse locks.

FIG. 6 shows a plan view of a spiral spring 5 with Euler spiral turns, that is to say a linear spiral geometry. Four spiral turns in total are provided, each with three and a half windings, such that the relatively large surface of the spiral turns permits a relatively smooth adjustability and rotatability of the spiral spring 5. In FIG. 6a, in which a section along the line A-A from FIG. 6 is shown, the arrangement of the spiral spring 5 between two contact surfaces 6, 7 can be seen. The outer circumference of the spiral spring 5 is provided with bores 55, which in the present case lie symmetrically opposite one another and through which the fastening screws or bolts 51 can be guided in order to secure the spiral spring on the lower part 3. FIG. 6a shows the wedge angle α of the spiral spring 5, which is between 10° and 50°, more particularly approximately 30°. The wedge angle α is the same wedge angle formed between the contact surfaces 6, 7.

If the spiral spring tapers in the radial direction, instead of the formation shown in FIGS. 6a and 6c, there is a funnel-shaped design relative to the rotation axis 4, and the wedge angle α is oriented the other way round.

FIG. 6b shows an enlarged detail view of the area B from FIG. 6a.

FIG. 7 shows a plan view of a spiral spring 5 with a nonlinear spiral geometry. The spiral spring 5 has four spiral turns with a winding length of approximately 225°, resulting in a substantially stiffer spring characteristic than in the spiral spring 5 of FIG. 6. The spiral spring 5 according to FIG. 7 also has bores 55 distributed about the circumference of the spiral spring 5, in this case in a greater number than in the spiral spring 5 according to FIG. 6. Smaller bores 56 are provided to save material, although they can also be used together with bolts to transmit moments. FIG. 7a shows the wedge angle α or the wedge angle of the contact surfaces 6, 7 (not shown) relative to each other. FIG. 7c shows the cup-like depression toward the rotation axis 4.

In a partial sectional view similar to that of FIG. 5, FIG. 8 shows an alternative embodiment of the joint device, in which splines 30, 530 are included on the lower part 3 and the cover 53, into which friction plates 531, 532, 533, 31, 32, 33 are guided in an axially displaceable and rotationally fixed manner. Instead of the spline 30, bolts or other positive connection elements can be provided. The rotationally fixed mounting can be produced by an interlocking of projections on the circumference of the plates 31, 32, 33, 531, 532, 533 and grooves and notches in the lower part 3 and cover 53. Between the friction plates 31, 32, 33, 531, 532, 533 on the side of the joint device facing the upper part 2, bolts 16, 17 transmit moments in the contact surfaces 6, 7 and the bracket 21 and the upper part 2. Friction plates 71, 72, 62, 63 are fitted onto these bolts 16, 17, resulting in an axially displaceable and moment-resistant connection. The bolts 16, 17 are pressed into the contact surfaces 6, 7. If the spiral spring 5 is turned in the direction of winding, the spiral spring turns bear on the contact surfaces 6, 7 and press these outward. By virtue of the axial mobility and the moment-resistant mounting in the lower part 3 and on the upper part 2 (not shown), the plate stacks are in this way pressed onto one another and prevent a rotation movement of the upper part 2 relative to the lower part 3, or make such a movement difficult. A final friction pairing is provided by the surface between an output part 73, 64, assigned to the upper part 2, and the cover 53 or lower part 3.

In the embodiment shown, a total of 16 friction surface pairings are made available, thus allowing the friction surface to be greatly increased. The more plates that are provided, the greater the friction surface. In an embodiment of the joint device with the plate stacks, it is also possible to have an arrangement of several spiral springs, if appropriate oppositely oriented windings. Applications are also possible in slipping components.

The invention claimed is:

1. A joint device for orthoses or prostheses comprising an upper part, a lower part pivotally mounted to the upper part about a pivot axis, and braking means that brakes or blocks a pivoting movement of the lower part relative to the upper part, wherein the braking means includes a spiral spring arranged between two contact surfaces, which is mounted such that when the spiral spring is braced in a direction of the contact surfaces about a rotation axis parallel to the pivot axis, side flanks of the spiral spring contact the contact surfaces.

2. The joint device as claimed in claim 1, wherein the rotation axis coincides with the pivot axis.

3. The joint device as claimed in claim 1, wherein the contact surfaces have a radially conical or radially curved contour.

4. The joint device as claims in claim 3, wherein the spiral spring is contoured in a manner corresponding to the contour of the contact surfaces.

5. The joint device as claimed in claim 3 wherein a cone angle (α) of the contact surfaces is between 10° and 50°.

6. The joint device as claimed in claim 1, wherein the bracing of the spiral spring is adjustable.

7. The joint device as claimed in claim 1, wherein the spiral spring, in its starting position, is in contact with the contact surfaces.

8. The joint device as claimed in claim 1, wherein the spiral spring is coupled to an actuator that braces the spiral spring onto the contact surfaces in or counter to the direction of winding of the spiral.

9. The joint device as claimed in claim 8, wherein the actuator is a servomotor.

10. The joint device as claimed in claim 8, wherein the actuator is coupled to the spiral spring via a lever or a toothed wheel.

11. The joint device as claimed in claim 10, wherein the lever or the toothed wheel is spring-loaded in the direction of locking.

12. The joint device as claimed in claim 8, wherein the spiral spring, in its starting position, is pretensioned counter to the actuator in the direction of locking.

13. The joint device as claimed in claim 8, further comprising a sensor device that measures at least one of forces, moments and the angle of the upper and lower parts relative to each other, wherein the sensor is coupled to a control unit which, as a function of the measured variables, activates the actuator and braces the spiral spring.

14. The joint device as claimed in claim 8, wherein the actuator is controlled by a control unit via myoelectric signals.

15. The joint device as claimed in claim 8, further comprising a device for detecting the spatial orientation of at least one of the upper part and the lower part, which is coupled to the actuator.

16. The joint device as claimed in claim 8, further comprising a device for detecting accelerations of at least one of the upper part and lower part of the joint device, or of the prosthesis or orthosis secured thereto, which is coupled to the actuator.

17. The joint device as claimed in claim 1, wherein at least one contact surface is mounted to be axially displaceable.

18. The joint device as claimed in claim 1, wherein the spiral spring includes multiple turns.

19. The joint device as claimed in claim 1, wherein the spiral spring has a nonlinear spiral geometry.

20. The joint device in claim 1, wherein the contact surfaces are coupled to an arrangement of plates, which increase the number of friction surfaces that the spiral spring is configured to contact.

* * * * *

UNITED STATES PATENT AND TRADEMARK OFFICE
CERTIFICATE OF CORRECTION

| | | |
|---|---|---|
| PATENT NO. | : 7,935,153 B2 | Page 1 of 1 |
| APPLICATION NO. | : 12/293319 | |
| DATED | : May 3, 2011 | |
| INVENTOR(S) | : Roland Auberger | |

It is certified that error appears in the above-identified patent and that said Letters Patent is hereby corrected as shown below:

In the Title page, the Assignee "Otto Bock Healthcare IP GmbH & Co. KG" should read --Otto Bock HealthCare GmbH--.

Signed and Sealed this

Thirty-first Day of January, 2012

David J. Kappos
*Director of the United States Patent and Trademark Office*